US006852280B2

(12) United States Patent
Vijay et al.

(10) Patent No.: US 6,852,280 B2
(45) Date of Patent: Feb. 8, 2005

(54) CONDENSED PERFUSION CIRCUIT FOR CARDIOPULMONARY BYPASS AND CARDIOPLEGIA

(76) Inventors: Venkataramana Vijay, 177 White Plains Rd., Apt. 86 D, Tarrytown, NY (US) 10591; Kevin McCusker, 188 Gosport Rd., Portsmouth, NH (US) 03801

( * ) Notice: Subject to any disclaimer, the term of this patent is extended or adjusted under 35 U.S.C. 154(b) by 53 days.

(21) Appl. No.: 10/403,567

(22) Filed: Mar. 31, 2003

(65) Prior Publication Data

US 2004/0191117 A1 Sep. 30, 2004

(51) Int. Cl.[7] .......................... A61M 1/36; A61M 37/00
(52) U.S. Cl. ....................... 422/45; 604/6.14; 604/6.16
(58) Field of Search .............................. 604/6.13, 4.01, 604/5.01, 6.01, 6.09, 6.1, 6.11, 6.14–6.16, 131, 141, 151, 19; 422/47, 48; 261/1–5, 75, 158–159; 96/4, 6–8, 10, 243; 435/2, 283.1, 284.1; 424/44–46; 600/16

(56) References Cited

U.S. PATENT DOCUMENTS

| | | | |
|---|---|---|---|
| 4,026,669 A | 5/1977 | Leonard et al. ................ | 23/258 |
| 4,466,804 A | 8/1984 | Hino .............................. | 604/4 |
| 4,529,397 A | 7/1985 | Hennemuth et al. ............ | 604/4 |
| 4,850,954 A | 7/1989 | Charvin ......................... | 604/4 |

(List continued on next page.)

OTHER PUBLICATIONS

"Isolated Extra–Corporeal Coronary Perfusion Circuit for Use During Off–Pump Coronary Artery Bypass Grafting" by K. McCusker et al., The Journal of Extra–Corporeal Technology, vol. 32, No. 3, Sep. 2000.
MAST System: a New Condensed Cardiopulmonary Bypass Circuit for Adult Cardiac Surgery by K. McCusker et al., Perfusion 2001, No. 16, pp 447–452.
"Cardiopulmonary Equipment", COBE Cardiovascular Inc., 2001, downloaded from web–site www.cobecv.com.
MAST System: A New Condensed Cardiopulmonary Bypass Circuit for Adult Cardiac Surgery; K Mcusker, V. Vijay, W. DeBois, R. Helm and D. Sisto; May, 2001.

*Primary Examiner*—Patricia Bianco
(74) *Attorney, Agent, or Firm*—Gordon & Jacobson, PC

(57) ABSTRACT

A total condensed circuit for cardiopulmonary bypass and cardioplegia are provided, as well as methods of using the same. The total circuit includes a cardiopulmonary bypass portion including tubing and components which together have a substantially short path length and priming volume preferably under 800 ml. Thus, the opportunity for an inflammatory response caused by blood contacting plasticizers is minimized. The bypass circuit includes a shunt which bypasses a blood reservoir of the total circuit. The cardioplegia circuit infuses cardioplegia fluid into blood pulled from an oxygenator of the bypass circuit. According to the method, either or both of heart-lung bypass and cardioplegia can be performed with only minimal or no isotonic priming solution circulated into the patient. In addition, use of the shunt and reservoir together eliminate the possibility of air entering the circulation system upon kinking of the circuit.

31 Claims, 4 Drawing Sheets

U.S. PATENT DOCUMENTS

| | | | |
|---|---|---|---|
| 5,263,924 A | 11/1993 | Mathewson | 604/4 |
| 5,270,005 A | 12/1993 | Raible | 422/46 |
| 5,358,481 A | 10/1994 | Todd et al. | 604/4 |
| 5,766,480 A | 6/1998 | Cosentino et al. | 210/644 |
| 5,823,986 A * | 10/1998 | Peterson | 604/6.09 |
| 5,958,338 A | 9/1999 | Lindsay et al. | 422/45 |
| 6,071,258 A | 6/2000 | Dalke et al. | 604/5 |
| 6,290,665 B1 | 9/2001 | Utterberg | 604/4.01 |
| 6,306,346 B1 | 10/2001 | Lindsay | 422/45 |
| 6,315,751 B1 | 11/2001 | Cosgrove et al. | 604/5.01 |
| 6,344,139 B1 | 2/2002 | Utterberg | 210/232 |
| 6,443,922 B1 | 9/2002 | Roberts et al. | 604/4.01 |
| 6,468,473 B1 | 10/2002 | Lindsay | 422/45 |
| 6,517,508 B1 | 2/2003 | Utterberg et al. | 604/4.01 |
| 6,613,008 B2 | 9/2003 | Aboul-Hosn et al. | 604/5.01 |
| 2002/0044889 A1 | 4/2002 | Aboul-Hosn et al. | 422/45 |
| 2002/0085952 A1 | 7/2002 | Ellingboe et al. | 422/45 |
| 2002/0087170 A1 | 7/2002 | Kuhns et al. | 604/5.01 |
| 2002/0176797 A1 | 11/2002 | Roberts et al. | 604/6.14 |
| 2003/0204127 A1 | 10/2003 | Rawles et al. | 600/16 |
| 2003/0208097 A1 | 11/2003 | Aboul-Hosn et al. | |

* cited by examiner

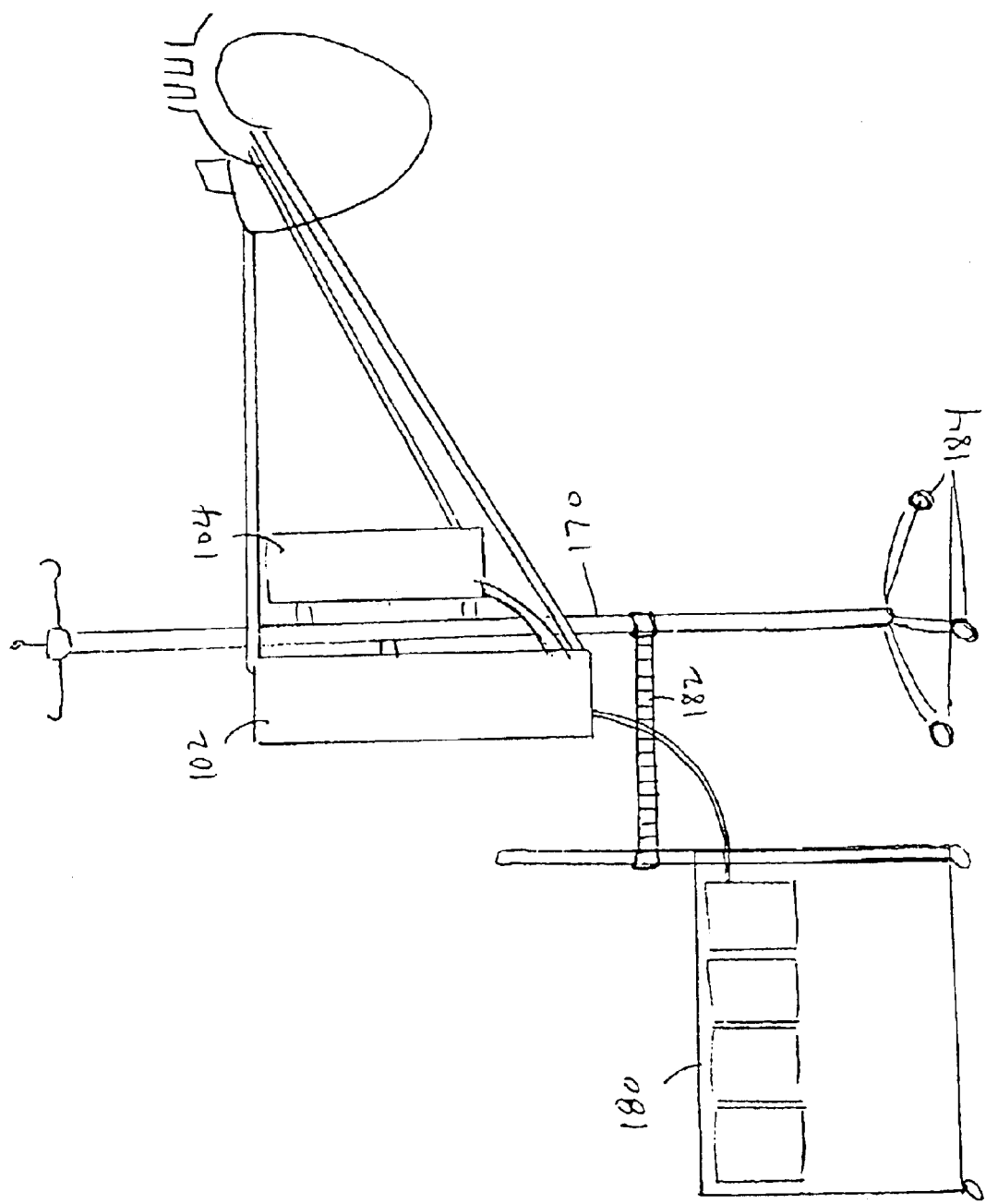

CONDENSED PERFUSION CIRCUIT FOR CARDIOPULMONARY BYPASS AND CARDIOPLEGIA

BACKGROUND OF THE INVENTION

1. Field of the Invention

This invention relates broadly to medical systems. More particularly, this invention relates to perfusion circuits for cardiopulmonary bypass and cardioplegia and methods of using the same.

2. State of the Art

In conventional open-heart surgery, the patient's breast bone is sawed open, the chest is spread apart with a retractor, and the heart is accessed through the large opening created in the patient's chest. The patient is placed on cardiopulmonary bypass and the patient's heart is then arrested using catheters and cannulae which are inserted directly into the large arteries and veins attached to the heart through the large opening in the chest.

Referring to prior art FIG. 1, the prior art bypass perfusion circuit 10 includes an arterial cannula 12 typically passed through the wall of the ascending aorta 14. A venous cannula 16 is passed through the right atrium 18 for withdrawing blood from the patient. The venous cannula 16 is coupled to an approximately eight foot length of ½ inch diameter polyvinyl chloride (PVC) tubing 20 (volume of 304 ml). All prior art systems have mandated the use of at least ½ inch diameter tubing at this location in order to ensure proper blood flow. Tubing 20 leads to a blood reservoir 22 adapted to store a blood volume of 300 to 600 ml. A one foot length of ⅜ inch diameter tubing 24 (volume of 21 ml) couples the reservoir 22 to a centrifugal pump 26 which has a volume of 80 ml. The centrifugal pump 26 is connected to a heart/lung console (not shown) which power the pump. A one foot length of ⅜ inch diameter tubing 28 (volume of 21 ml) transfers blood from the pump 26 to an oxygenator 30 (volume 280 ml). Another one foot length of ⅜ inch diameter tubing 32 (volume of 21 ml) transfers blood from the oxygenator 30 to a forty micron arterial filter 34 (volume of 50 ml). The arterial filter 34 is adapted to capture gaseous and fatty embolisms. From the filter 34, an eight foot length of ⅜ inch diameter tubing 36 (volume 168 ml) completes the circuit back to the arterial cannula 12. The reservoir 22, oxygenator 30, and arterial filter 34 are an integrated unit 38. Nevertheless, tubings 24, 28, 32 are required to connect the various sections thereof. Blood is pulled from the patient through the venous cannula 16, circulated through the tubing, reservoir, pump, oxygenator and filter, which are together referred to as the perfusion circuit 10, and back to the patient through the arterial cannula 12. The entire bypass circuit 10 is mounted on a pole fixed to the console (now shown) which powers the centrifugal pump 26, and is thus constrained to the location of the console.

Prior to use, the two lengths of eight foot tubing 20, 36 of the circuit 10 are coupled together at a pre-bypass filter (not shown) having an 80 ml volume. One length of the tubing is then decoupled from about the pre-bypass filter and the circuit is primed with an isotonic solution, e.g., saline, to remove air and any other impurities from within the components and tubing. The priming volume is relatively high, calculated from the above stated individual volumes of the tubing and components to be approximately 1325 to 1625 ml (not including the cannulae). Note that the ½ inch diameter tubing has a volume of 38 ml/foot, and ⅜ inch diameter tubing has a volume of 21 ml/foot.

After the perfusion circuit 10 is primed with saline, the pre-bypass filter is removed and respective ends of the circuit are coupled to the arterial and venous cannulae 12, 16.

Referring to prior art FIG. 2, a cardioplegia circuit 40 is then coupled to the heart. The cardioplegia circuit 40 generally includes a roller pump 42 which pulls blood from the oxygenator and feeds the blood into the heart. To the circuit 40, cardioplegia fluid 44 is added. The cardioplegia fluid 44 is generally potassium suspended in a one liter isotonic solution. A length of flexible tubing 46 extends from the roller pump 42 to a bubble trap 48 and a catheter 50 extending from the bubble trap 48 into the heart 15. The components and tubing of the cardioplegia circuit must also be primed with approximately 300 to 400 ml of an isotonic solution to remove air and foreign matter prior to use. After priming, the roller pump 42 is operated to induce cardioplegia.

Once the perfusion circuit pump is operated, cardioplegia is induced and the patient's blood is oxygenated outside the body and circulated back to the patient. When the perfusion pump is operated, the priming saline is also circulated through the patient's body.

This standard procedure is undesirable for several reasons. First, the relatively large priming volume, and particularly the length of tubing, of the system requires that the patient's blood come into contact with a large non-vascular surface area for a relatively long period of time. When blood contacts plasticizer components such as the tubing, there tends to be an inflammatory response by the body. This is so even when the tubing and other components are coated with modern anti-inflammatory coatings. This response can compromise the recovery of the patient.

Second, there are instances in prior art perfusion circuits where a section of the tubing or cannulae kinks, inhibiting blood flow through the perfusion circuit. In such a situation, the pump may draw in air through the reservoir, which is open to the atmosphere, and circulate the air into the patient's vascular system. This is extremely dangerous to the patient and may even be deadly.

Third, the large amount of isotonic fluid required for priming the perfusion bypass and cardioplegia circuits is circulated into the patient's body in addition to units of blood that may have been administered to the patient prior to the procedure. This extraordinary volume of fluid in the human body taxes the patient, as the kidneys are forced to process a substantial amount of additional fluid.

SUMMARY OF THE INVENTION

It is therefore an object of the invention to provide a perfusion bypass circuit that minimizes priming volume.

It is another object of the invention to provide a perfusion circuit that prevents air from being pumped through the circuit in the event of cannulae or tubing kinks.

It is a further object of the invention to provide a combined perfusion and cardioplegia circuit that minimizes priming volume.

It is also an object of the invention to provide a method of using a perfusion circuit for cardiopulmonary bypass in which no priming liquid is circulated through the body.

It is an additional object of the invention to provide a method of using a perfusion circuit for cardiopulmonary bypass in which air is prevented from being circulated into the patient, even if a section of tubing or a cannulae is temporarily or permanently closed.

It is still another object of the invention to provide a method of introducing cardioplegia fluid which introduces relatively little, if any, additional isotonic fluid to the patient.

In accord with these objects, which will be discussed in detail below, a perfusion circuit for cardiopulmonary bypass and cardioplegia, and methods of using the same, are provided. The perfusion circuit includes a bypass portion including tubing and components which together have a substantially shorter path length and priming volume than prior art bypass perfusion circuits. The total priming volume of the bypass circuit in the preferred embodiment is under 800 ml, and more preferably under 700 ml. This reduction in priming volume is partially effected by reducing the volume of blood which will be pooled in the reservoir, as discussed below. As the length and volume of the circuit is relatively shorter and smaller than the prior art, there is reduction in the inflammatory response caused by blood contacting plasticizers.

According to another preferred aspect of the invention, a shunt is provided to connect the venous side one foot length of tubing with the pump. The shunt bypasses the reservoir. A releasable clamp is provided for the shunt. Releasable clamps are provided before and after the reservoir to prevent blood flow thereto or therefrom when the shunt is opened.

According to another preferred, but optional, aspect of the invention, a condensed cardioplegia circuit is provided. The cardioplegia circuit includes a roller pump having an input coupled to an output port of the oxygenator, and an output coupled to a bubble trap by a very short piece of tubing. A catheter is coupled to the bubble trap and includes a needle at its end which is inserted into the heart. In accord with the invention, an infusion pump is provided which infuses concentrated cardioplegia fluid into the circuit, without necessitating large volumes of isotonic solution which would otherwise be pumped into the patient. Thus, the circuit described is a total circuit for both bypass and cardioplegia.

In accord with a preferred method of the invention, the circuit is primed with a saline and operated to circulate the saline through the pre-bypass filter. After circulation of the saline, the venous-side and arterial-side tubings are separated from the pre-bypass filter, and coupled to respective venous and arterial cannulae which are inserted into the heart.

The saline is then replaced with the patient's own blood. That is, blood is pulled from the venous and arterial sides into the bypass circuit and the saline is drained by disconnecting tubing from a component or via a valve. This is permissible due to the small priming volume of the bypass circuit. In prior art systems, a sufficiently large volume of priming solution is required such that it would not be medically safe to prime the circuit with the patient's blood. Where the patient's blood can be the priming fluid, none of the negative side effects associated with circulating a large volume of non-blood fluid through the body results. Preferably, 0 to 100 ml of blood is pooled in the reservoir.

Once the bypass circuit is primed with blood, the bypass circuit is activated. The bypass circuit circulates the patient's blood from the reservoir through the oxygenator and the arterial filter, and then back to the patient.

Then, the cardioplegia roller pump pulls blood from the oxygenator, and sends it through the bubble trap. The blood in the cardioplegia circuit is infused with cardioplegic fluid from the infusion pump and circulated to the heart. Practically no saline solution is required for the cardioplegia portion of the total circuit. In addition, all saline solution can be eliminated from entering the patient by also replacing the saline solution in the cardioplegia circuit with blood prior to operating the infusion pump.

According to one preferred aspect of the invention, where a patient has sufficient blood, such as when additional blood units have been administered prior to the procedure, the reservoir is permitted to pool a reserve of blood. Then the shunt clamp is opened and the reservoir clamps are closed to remove the blood in the reservoir from the circulation. The perfusion pump then pulls blood directly from the patient and through the shunt, while bypassing the reservoir. Then, if any of the tubing on the arterial side of the pump kinks, the venous cannula will apply suction against the heart tissue and close circulation. No air can enter from the reservoir. Moreover, if any of the tubing on the venous side of the pump kinks, the physician or perfusionist can release the reservoir clamps and again allow the pump to pull blood from the reservoir until the kinking can be resolved. If any blood remains in the reservoir at the end of the bypass procedure, the reservoir clamp can be released and the arterial side of the circuit may be clamped close to cause substantially all of the reservoir blood to be reintroduced into the patient.

From the foregoing, it is appreciated that a condensed and safe circuit is provided for bypass and cardioplegia.

Additional objects and advantages of the invention will become apparent to those skilled in the art upon reference to the detailed description taken in conjunction with the provided figures.

BRIEF DESCRIPTION OF THE DRAWINGS

Prior art

Prior art

FIG. 4 is a schematic illustration of the total condensed circuit of FIG. 3 mounted on a pole which is coupled to a heart/lung console with an articulating arm.

DETAILED DESCRIPTION OF THE PREFERRED EMBODIMENTS

Figure 1:
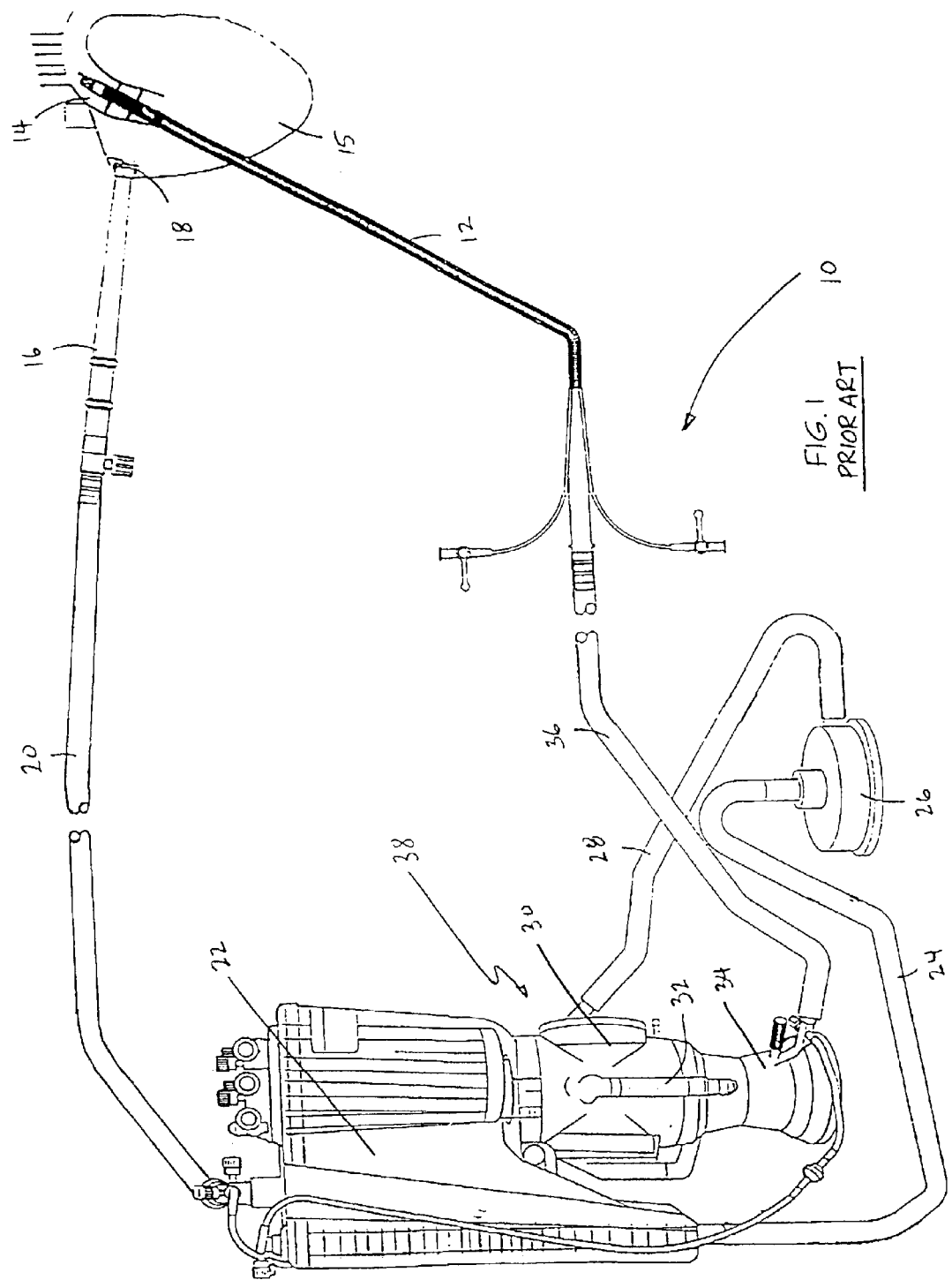
FIG. 1 illustrates a prior art bypass perfusion circuit.
Figure 2:
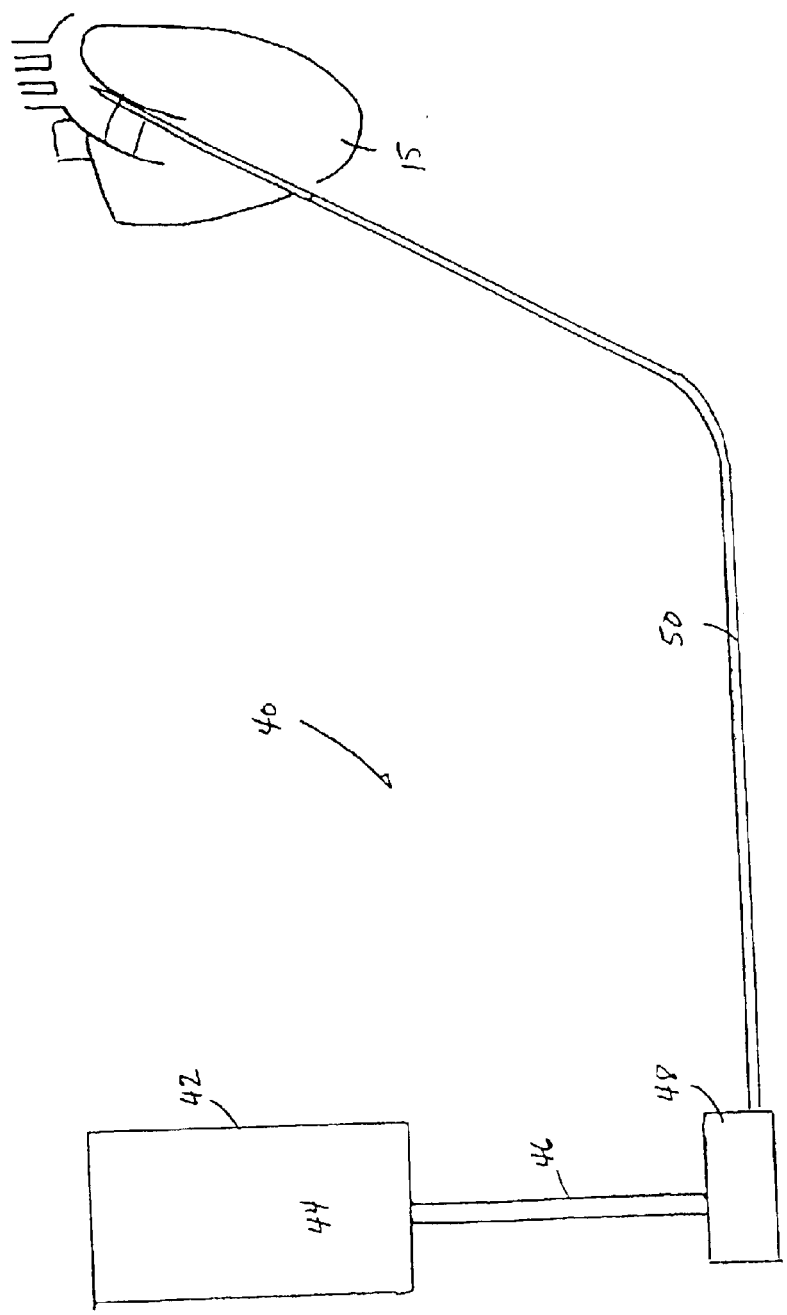
FIG. 2 illustrates a prior art cardioplegia perfusion circuit.
Figure 3:
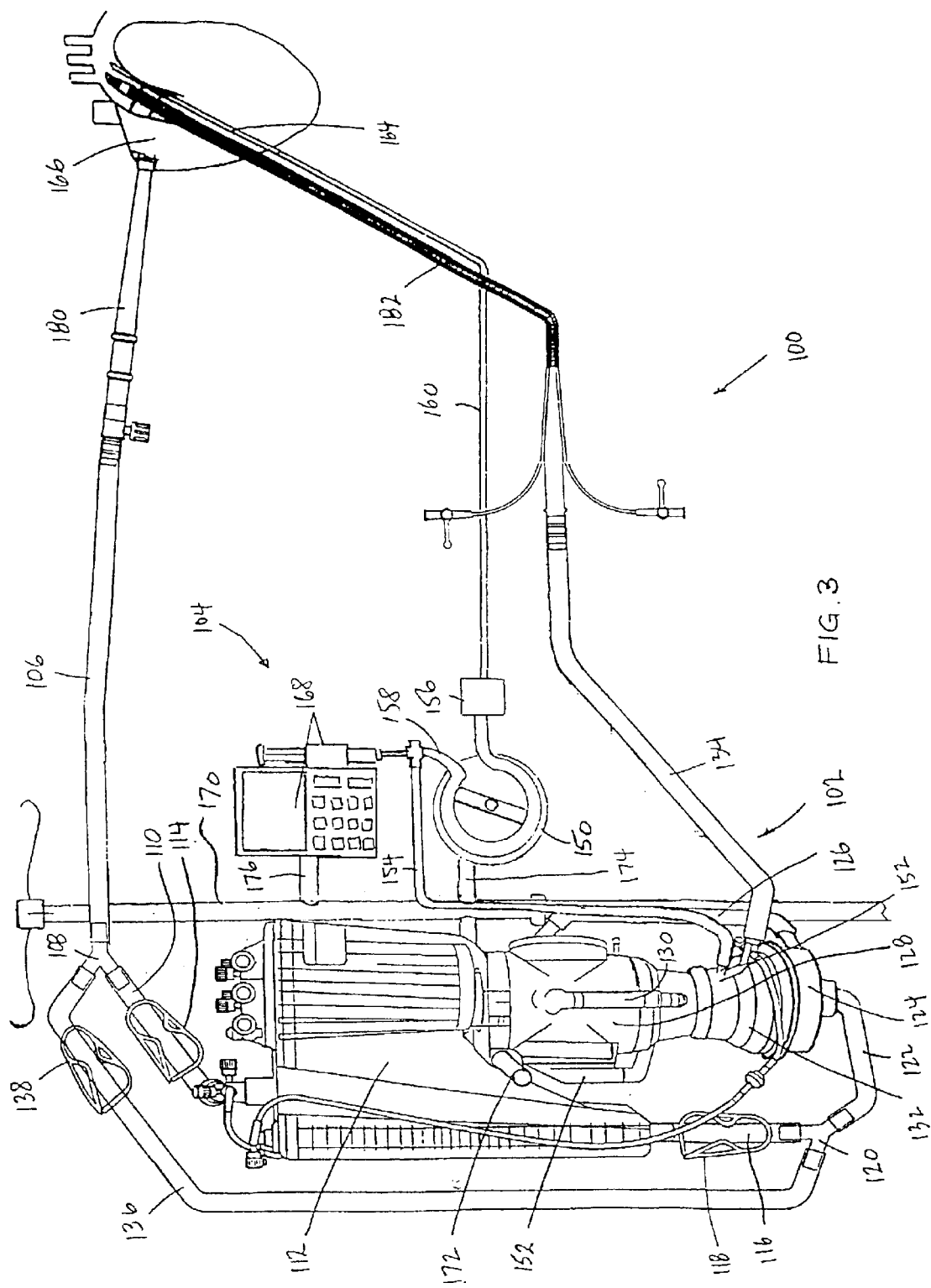
FIG. 3 illustrates a total condensed circuit according to the invention which provides bypass and cardioplegia perfusion.

Turning now to FIG. 3, a low priming volume combined heart-bypass and cardioplegia circuit, hereinafter referred to as a total condensed circuit 100, is shown. The circuit 100 includes bypass portion 102 and a cardioplegia portion 104, which will be described in detail below.

The bypass portion 102 includes a venous-side approximately one foot long ⅜ inch diameter PVC tubing 106 (volume of 21 ml) which leads to a first Y-connector 108. From the Y-connector 108, an approximately three inch length of ⅜ diameter tubing 110 (volume 5 ml) is coupled to a blood reservoir 112 (which as discussed below will preferably hold 0 to 100 ml of blood). Tubing 110 is provided with a releasable clamp 114. Another short three inch length of ⅜ inch diameter tubing 116 (volume 5 ml), provided with a releasable clamp 118, extends from the reservoir 112 and is coupled to a second Y-connector 120. Another short three inch length of ⅜ inch diameter tubing 122 (volume 5 ml) extends from the second Y-connector 120 to a first perfusion pump 124 (volume 80 ml), thereby placing the reservoir 112 and the pump 124 in fluid communication. A six inch length of ⅜ inch diameter tubing 126

(volume 10 ml) transfers blood from the pump 124 to an oxygenator 128 (volume 280 ml). Another six inch length of ⅜ inch diameter tubing 130 (volume 10 ml) transfers blood from the oxygenator 128 to an arterial filter 132 (volume 50 ml). In order to use such a short length of tubing between the pump 124 and the oxygenator 128, the location of the pump 124 is relocated adjacent the arterial filter 132. An arterial-side one foot length of ⅜ inch diameter tubing 134 (volume 21 ml) extends from the arterial filter 132. Prior to priming, the venous- and arterial-side tubing 106, 134 are coupled at a pre-bypass filter (not shown, volume 80 ml). Therefore, the total priming volume of the bypass circuit 102 in a preferred embodiment is under 800 ml, more preferably under 700 ml, and most preferably between approximately 567 to 670 ml. This reduction in priming volume is effected by reducing the diameter of the venous side tubing (contrary to prior art teachings), reducing the length of the tubing, relocating the components relative to the each other, and reducing the volume of blood which will be pooled in the reservoir, as discussed with respect to the method described below. As the length and volume of the bypass circuit is relatively shorter and smaller than the prior art, there is less opportunity for an inflammatory response caused by blood contacting plasticizers.

The bypass circuit 102 is preferably, though optionally, provided with a shunt 136. The shunt 136 is preferably a twelve to eighteen inch length of ⅜ inch diameter tubing (volume 20 to 30 ml) connecting the first Y-connector 108 with the second Y-connector 120 and thereby bypassing the reservoir 112. A releasable clamp 138 is provided on the shunt 136. The use of the shunt 136 is described below with respect to the method of the invention.

The cardioplegia circuit 104 includes a relatively short length of 3/16 to ¼ inch diameter tubing 154 coupled to an output port 152 of the oxygenator 128. Tubing 154 or a tubing 158 coupled thereto extends through a roller pump 150 which is adapted to move rollers against the tubing to thereby pull blood into the tubing and move it therethrough. After the tubing 158 exits the roller pump 150, it is coupled to a bubble trap 156. A catheter 160 is coupled to the bubble trap 156, and a needle 164 is provided at the end of the catheter 160 and is adapted to be inserted into the heart 166. The circuit 104 also includes an infusion pump 168 which slowly infuses a small volume of highly concentrated cardioplegic fluid (e.g., potassium in solution) into the tubing 158. Preferably, only 5 to 40 ml of the concentrated cardioplegia fluid is introduced into the patient over the course of the bypass procedure, as opposed to 1 to 2 liters of cardioplegic solution in the prior art. As the tubing 154, 158 and catheter 160 are adapted to carry the patient's own blood from the oxygenator 128, the infusion pump 168 is adapted to infuse the concentrated cardioplegic fluid into the blood. This cardioplegia circuit has minimal priming volume, preferably no more than 30 to 40 ml.

The bypass circuit 102 is vertically mounted on a pole 170 with bar 172. The cardioplegia circuit 104 is mounted on the pole 170 at bars 174 and 176. The pole is self-supporting on wheels 184. Other mounting means may certainly be used. However, it is desirable that any mounting means permit the bypass circuit 102 and the cardioplegia circuit 104 to be located as close to the patient as possible to minimize the length of the tubing of the circuits.

Referring to FIG. 4, according to one preferred embodiment of the invention, the pole 170 is coupled to the heart/lung console 180 by an articulating arm 182. The console 180, among other functions, powers the centrifugal pump 124 and provides controls therefor. The arm 182 maintains a structural relationship between the circuits 102, 104 and the console 180, while permitting a wide range of movement of the circuits relative to the console. Thus, the relatively large footprint console 180 can be located away from the patient to permit physician access to the patient, and the relatively small footprint of the pole 170 can be moved on its wheels 184 adjacent the patient, thereby permitting the very short tubing lengths of tubes 106 and 134. The arm 182 ensures that the pole 170 is not moved too far relative to the console 180, i.e., the pole is not moved a distance which may cause inadvertent disconnect between the centrifugal pump 124 and the console 180. Furthermore, the arm 182 provides a psychological benefit in that the circuits 102, 104 and console 180 maintain the appearance of an integrated unit. Alternatively, a preferably cantilevered swing-arm (not shown) mounted to the console may be provided, and the circuits 102, 104 can be mounted to a pole which is supported by the swing-arm. This system also permits the circuits to be located at a distance relative to the console and, more importantly, closer to the patient.

Referring back to FIG. 3, in accord with a preferred method of the invention, the bypass circuit is primed with an isotonic priming solution, e.g. saline, which is circulated by the pump 124 through the pre-bypass filter. After priming and circulation, the venous-side and arterial-side tubings 106, 134 are separated from the pre-bypass filter (not shown). The pre-bypass filter is then removed and venous and arterial cannulae 180, 182 are coupled to the respective venous- and arterial-side tubing 106, 134 and inserted into the heart 166.

In accord with a preferred aspect of the invention, the isotonic solution is then replaced with the patient's own blood. That is, using gravity or vacuum-assist, blood is pulled into the venous and arterial sides of the bypass circuit 102 and the saline is released by disconnecting tubing from a component (e.g., at tubing 122 and at tubing 134) or via a valve. This is permissible due to the small priming volume of the bypass circuit 102. In prior art systems, a sufficiently large volume of priming solution is required such that it would not be medically safe to prime the circuit with the patient's blood. However, in the present invention, since the patient's blood can be the priming fluid, none of the negative side effects associated with circulating a large volume of non-blood fluid through the body results. Preferably, in addition to priming the circuit, 0 to 100 ml of blood is pooled in the reservoir 112. This is also in contradiction to prior art methodology, where it is standard to pool at least 300 ml, and up to 600 ml, of blood during operation of the bypass circuit.

Once the bypass circuit 102 is primed with blood, the bypass circuit is activated. The pump 124 in the bypass circuit 102 circulates the patient's blood from the reservoir 112 to the oxygenator 128, the arterial filter 132, and then back to the patient through the arterial-side tubing 134 and cannula 182.

After bypass is activated, cardioplegia is induced. This is effected via the condensed cardioplegia circuit 104, in which the perfusion roller pump 150 pulls blood from the oxygenator 128, and sends it through the bubble trap 156 and then to the heart of the patient. The blood in the circuit, e.g., either before the roller pump 150 or exiting the bubble trap 156, is infused with cardioplegic fluid (concentrated potassium in solution) from the infusion pump 168 and circulated to the heart 166. Practically no isotonic priming solution is required for the cardioplegic portion of the total circuit 100. In addition, all priming solution can be eliminated from the patient by replacing the priming solution in the cardioplegic circuit 104 with blood prior to operating the perfusion pump 150 and infusion pump 168. In this manner, the patient's own blood is the primary carrier for the cardioplegia fluid.

According to one preferred aspect of the invention, where a patient has sufficient blood, such as when additional blood units have been administered prior to the procedure, the reservoir 112 is permitted to pool a reserve of blood, e.g., up to approximately 3000 ml, although the amount of stored blood volume is dependent upon the flow and oxygenation needs of the patient during the procedure. Then the shunt clamp 138 is opened and the reservoir clamps 114, 118 are closed to remove the blood in the reservoir 112 from circulation. The bypass perfusion pump 124 then pulls blood directly from the patient and through the shunt 136, while bypassing the reservoir 112. Then, if any of the tubing on the arterial side of the pump 124 or the arterial cannula 182 kinks, the venous cannula 180 will apply suction against the heart tissue 166 and close circulation. No air can enter from the reservoir 112; thus, no air can be circulated into the patient. Moreover, if any of the tubing 106 on the venous side of the pump 124 kinks such that blood flow through the shunt is limited or prevented, the physician or perfusionist can release the reservoir clamps 114 and 118 and again allow the pump 124 to pull blood from the reservoir 112 until the kinking can be resolved.

If any blood remains in the reservoir at the end of the bypass procedure, the reservoir clamp can be released and the arterial side of the circuit may be clamped close to cause substantially all of the reservoir blood to be reintroduced into the patient.

From the foregoing, it is appreciated that a condensed and safe circuit is provided for bypass and cardioplegia.

There have been described and illustrated herein embodiments of a total condensed circuit, i.e., a combined bypass and cardioplegia circuit of substantially small priming volume, and methods of heart-lung bypass and inducing cardioplegia. While particular embodiments of the invention have been described, it is not intended that the invention be limited thereto, as it is intended that the invention be as broad in scope as the art will allow and that the specification be read likewise. Thus, while a total condensed circuit has been disclosed, it will be appreciated that the bypass circuit may be constructed and used without the cardioplegia circuit. Moreover, while a circuit having the low priming volumes described is preferred where the patient's blood is used to prime the circuit, it should be understood that any method of bypass and/or cardioplegia where the patient's blood is used to prime the circuit, regardless of the volume of the circuit, is within the scope of the invention. In addition, while one foot long sections are tubing are provided for coupling the venous and arterial sides of the circuit to the respective cannulae, it is appreciated that longer tubing, e.g., up to approximately two feet, may be used to facilitate placement of the circuit relative to the patient. Even by extending this tubing by such length, circuit. It will therefore be appreciated by those skilled in the art that yet other modifications could be made to the provided invention without deviating from its spirit and scope as claimed.

What is claimed is:

1. A cardiopulmonary bypass circuit for oxygenating blood outside a patient and circulating oxygenated blood through the patient, said circuit comprising:

a) a blood reservoir;
b) a perfusion pump in fluid communication with said reservoir;
c) a blood oxygenator in fluid communication with said pump;
d) an arterial filter in fluid communication with said oxygenator;
e) a first length of tubing located to place said reservoir in venous-side fluid communication with the patient;
f) a second length of tubing located to place said arterial filter in arterial-side fluid communication with the patient;
g) a shunt placing said first length of tubing and said pump in fluid communication and bypassing said blood reservoir;
h) manual selecting structure which permits selection of one of said shunt and said blood reservoir to be included in said circuit and the other of said shunt and said blood reservoir to be excluded from said circuit; and
i) structure external said reservoir which prevents any store of blood in said blood reservoir from being pulled by said perfusion pump when said blood reservoir is excluded from said circuit such that said perfusion pump pulls blood from said first length of tubing while bypassing the any store of blood in said blood reservoir, wherein said circuit has a priming volume of less than approximately 800 ml.

2. A circuit according to claim 1, further comprising:

j) a second perfusion pump;
k) a tubular member coupling said second perfusion pump and said oxygenator; and
l) an infusion pump adapted to infuse an injectate into fluid circulated by said second perfusion pump.

3. A circuit according to claim 2, wherein:

said second perfusion pump, said tubular member and said infusion pump define an infusion circuit with a priming volume of less than approximately 40 ml.

4. A circuit according to claim 1, wherein:

said priming volume of said circuit is less than approximately 700 ml.

5. A circuit according to claim 1, wherein:

said circuit has a priming volume of between 567 and 700 ml.

6. A cardiopulmonary bypass circuit for oxygenating blood outside a patient and circulating oxygenated blood through the patient, said circuit comprising:

a) a blood reservoir;
b) a perfusion pump;
c) a blood oxygenator;
d) an arterial filter in fluid communication with said oxygenator;
e) a first length of tubing located to place said blood reservoir in venous-side fluid communication with the patient;
f) a second length of tubing placing said blood reservoir and said pump in fluid communication;
g) a third length of tubing placing said pump and said oxygenator in fluid communication;
h) a fourth length of tubing placing said oxygenator and said arterial filter in fluid communication;
i) a fifth length of tubing located to said arterial filter in arterial-side fluid communication with the patient;
j) a shunt placing said first length of tubing and said pump in fluid communication and bypassing said blood reservoir;

k) manual selecting structure which permits selection of one of said shunt and said blood reservoir to be included in said circuit and the other of said shunt and said blood reservoir to be excluded from said circuit; and l) structure external said reservoir which prevents any store of blood in said blood reservoir from being pulled by said perfusion pump when said reservoir is excluded from said circuit such that said perfusion pump pulls blood from said first length of tubing while bypassing the any store of blood in said blood reservoir, wherein a pathway through said circuit has a priming volume of less than approximately 800 ml.

7. A circuit according to claim 6, further comprising:

m) a second perfusion pump;

n) a tubular member coupling said second perfusion pump and said oxygenator; and o) an infusion pump adapted to infuse an injectate into fluid circulated by said second perfusion pump.

8. A circuit according to claim 7, wherein:

said second perfusion pump, said tubular member and said infusion pump define an infusion circuit with a priming volume of less than approximately 40 ml.

9. A circuit according to claim 6, wherein:

said circuit has a priming volume of between 567 and 700 ml.

10. A cardiopulmonary bypass circuit for oxygenating blood outside a patient and circulating oxygenated blood through the patient, said circuit comprising:

a) a venous line;

b) a blood reservoir in fluid communication and in series with said venous line;

c) a perfusion pump in fluid communication and in series with said blood reservoir;

d) a blood oxygenator in fluid communication and in series with said pump;

e) an arterial filter in fluid communication and in series with said oxygenator;

f) a shunt placing said first length of tubing and said pump in fluid communication and bypassing said blood reservoir;

g) manual selecting structure which permits selection of one of said shunt and said blood reservoir to be included in said circuit and the other of said shunt and said blood reservoir to be excluded from said circuit; and h) structure external said reservoir which prevents any store of blood in said blood reservoir from being pulled by said perfusion pump when said blood reservoir is excluded from said circuit such that said perfusion pump pulls blood from said first length of tubing while bypassing the any store of blood in said blood reservoir, wherein said circuit has a priming volume of less than approximately 800 ml.

11. A circuit according to claim 10, further comprising:

i) an infusion system configured to infuse an injectate directly into blood oxygenated by said circuit.

12. A circuit according to claim 11 wherein:

said priming volume of said circuit is less than approximately 700 ml.

13. A circuit according to claim 11, wherein:

said circuit has a printing volume of between 567 and 700 ml.

14. A circuit according to claim 11, wherein:

said infusion system includes,
(i) a second perfusion pump,
(ii) a tubular member coupling said second perfusion pump and said oxygenator, and
(iii) an infusion pump adapted to infuse an injectate into fluid circulated by said second perfusion pump.

15. A cardiopulmonary bypass circuit for oxygenating blood outside a patient and circulating oxygenated blood through the patient, said circuit comprising:

a) a blood reservoir;

b) a perfusion pump;

c) a blood oxygenator;

d) a filter in fluid communication with said oxygenator;

e) an approximately one to two foot long ⅜ inch diameter tubing located to place said blood reservoir in venous-side fluid communication with the patient;

f) an approximately six inches of ⅜ inch diameter tubing placing said blood reservoir and said pump in fluid communication;

g) an approximately six inches of ⅜ inch diameter tubing placing said pump and said oxygenator in fluid communication;

h) an approximately one to two foot long ⅜ inch diameter tubing in fluid communication with said arterial filter; and i) a shunt located to place said perfusion pump in venous-side fluid communication with the patient and bypassing said blood reservoir.

16. A circuit according to claim 15, further comprising:

j) an infusion system configured to infuse an injectate directly into blood oxygenated by said circuit.

17. A circuit according to claim 16, wherein:

said infusion system includes, (i) a second perfusion pump, (ii) a tubular member coupling said second perfusion pump and said oxygenator, and (iii) an infusion pump adapted to infuse an injectate into fluid circulated by said second perfusion pump.

18. A circuit according to claim 15, wherein:

wherein said circuit has a priming volume of less than approximately 800 ml.

19. A circuit according to claim 15, wherein:

said circuit has a priming volume of less than approximately 700 ml.

20. A circuit according to claim 15, wherein:

said circuit has a priming volume of between 567 and 700 ml.

21. A circuit according to claim 15, further comprising:

j) manual selecting structure which permits selection of one of said shunt and said blood reservoir to be included in said circuit and the other of said shunt and said blood reservoir to be excluded from said circuit; and k) structure external said reservoir which prevents any store of blood in said blood reservoir from being pulled by said perfusion pump when said blood reservoir is excluded from said circuit such that said perfusion pump pulls blood from the patient while bypassing the any store of blood in said blood reservoir.

22. A cardiopulmonary bypass circuit for oxygenating blood outside a patient and circulating oxygenated blood through the patient, said circuit comprising:

a) a blood reservoir;

b) a perfusion pump;

c) a blood oxygenator;

d) a filter in fluid communication with said oxygenator;

e) a first tubing not exceeding approximately two feet in length and approximately ⅜ inch in diameter located to place said blood reservoir in venous-side fluid communication with the patient;

f) a second tubing not exceeding approximately six inches and approximately ⅜ inch in diameter and placing said blood reservoir and said pump in fluid communication;

g) a third tubing not exceeding approximately six inches in length and ⅜ inch in diameter and placing said pump and said oxygenator in fluid communication.

h) a fourth tubing not exceeding approximately two feet in length and approximately ⅜ inch in diameter and in fluid communication with said arterial filter; and i) a shunt located to place said perfusion pump in venous-side fluid communication with the patient and bypassing said blood reservoir.

23. A cardiopulmonary bypass circuit for oxygenating blood outside a patient and circulating oxygenated blood through the patient, said circuit comprising:

a) a blood reservoir;

b) a perfusion pump in fluid communication with said reservoir;

c) a blood oxygenator in fluid communication with said pump;

d) an arterial filter in fluid communication with said oxygenator;

e) a first length of tubing located to place said reservoir in venous-side fluid communication with the patient;

f) a second length of tubing located to place said arterial filter in arterial-side fluid communication with the patient;

g) a shunt placing said first length of tubing and said pump in fluid communication and bypassing said blood reservoir;

h) manual selecting structure which permits selection of one of said shunt and said blood reservoir to be included in said circuit and the other of said shunt and said blood reservoir to be excluded from said circuit; and i) structure external said reservoir which prevents any store of blood in said blood reservoir from being pulled by said perfusion pump when said blood reservoir is excluded from said circuit such that said perfusion pump pulls blood from said first length of tubing while bypassing the any store of blood in said blood reservoir.

24. A circuit according to claim 23, further comprising:

j) a second perfusion pump;

k) a tubular member coupling said second perfusion pump and said oxygenator; and l) an infusion pump adapted to infuse an injectate into fluid circulated by said second perfusion pump.

25. A cardiopulmonary bypass circuit for oxygenating blood outside a patient and circulating oxygenated blood through the patient, said circuit comprising:

a) a venous line;

b) a blood reservoir in fluid communication and in series with said venous line;

c) a perfusion pump in fluid communication and in series with said blood reservoir;

d) a blood oxygenator in fluid communication and in series with said pump;

e) an arterial filter in fluid communication and in series with said oxygenator;

f) a shunt placing said venous line and said pump in fluid communication and bypassing said blood reservoir;

g) manual selecting structure which permits selection of one of said shunt and said blood reservoir to be included in said circuit and the other of said shunt and said blood reservoir to be excluded from said circuit; and h) structure external said reservoir which prevents any store of blood in said blood reservoir from being pulled by said perfusion pump when said blood reservoir is excluded from said circuit such that said perfusion pump pulls blood from said venous line while bypassing the any store of blood in said blood reservoir.

26. A circuit according to claim 25, further comprising;

i) an infusion system configured to infuse an injectate directly into blood oxygenated by said circuit.

27. A cardiopulmonary bypass circuit for oxygenating blood outside a patient and circulating oxygenated blood through the patient, said circuit comprising:

a) a venous line;

b) a blood reservoir in fluid communication and in series with said venous line;

c) a perfusion pump in fluid communication and in series with said blood reservoir;

d) a blood oxygenator in fluid communication and in series with said pump;

e) an arterial filter in fluid communication and in series with said oxygenator;

f) a shunt placing said venous line and said pump in fluid communication and bypassing said blood reservoir; and g) structure external said reservoir which prevents any store of blood in said blood reservoir from being pulled by said perfusion pump when said blood reservoir is excluded from said circuit and said perfusion pump draws blood from the patient through said shunt such that said perfusion pump pulls blood from said venous line while bypassing the any store of blood in said blood reservoir.

28. A circuit according to claim 27, further comprising:

h) an infusion system configured to infuse an injectate directly into blood oxygenated by said circuit.

29. A circuit according to claim wherein:

said circuit has a priming volume of less than approximately 800 ml.

30. A circuit according to claim wherein:

said priming volume of said circuit is less than approximately 700 ml.

31. A circuit according to claim 27, wherein:

said circuit has a priming volume of between 567 and 700 ml.

* * * * *